United States Patent [19]
Andel

[11] Patent Number: 5,144,100
[45] Date of Patent: Sep. 1, 1992

[54] WIRE SEPARATOR APPARATUS

[76] Inventor: Gregory G. Andel, 2123 Shillings Chase Ct., Kennesaw, Ga. 30144

[21] Appl. No.: 636,191

[22] Filed: Dec. 31, 1990

[51] Int. Cl.⁵ .............................................. H01B 7/34
[52] U.S. Cl. .................................. 174/135; 174/72 A; 174/146; 128/696
[58] Field of Search ................. 174/135, 72 A, 72 TR, 174/146; 128/696, 710, 712, 731

[56] References Cited

U.S. PATENT DOCUMENTS

| | | | |
|---|---|---|---|
| D. 311,487 | 10/1890 | Platt | D8/396 |
| 733,876 | 7/1903 | Schulze . | |
| 804,365 | 11/1905 | Appleby | 174/146 |
| 2,264,408 | 12/1941 | Röhr et al. | 72/16 |
| 3,836,415 | 9/1974 | Hilderbrant | 156/296 |
| 3,895,635 | 7/1975 | Justus et al. | 128/696 X |
| 4,051,383 | 9/1977 | Dola | 174/72 A X |
| 4,353,372 | 10/1982 | Ayer | 128/696 X |
| 4,412,662 | 11/1983 | Rutecki | 242/125.3 |
| 4,874,908 | 10/1989 | Johansson | 174/72 A |
| 4,936,011 | 6/1990 | Berry et al. | 29/845 |
| 4,936,306 | 6/1990 | Doty | 128/731 X |

FOREIGN PATENT DOCUMENTS 0059172 9/1982 European Pat. Off. ............ 128/696

Primary Examiner—Leo P. Picard
Assistant Examiner—Hyung S. Sough
Attorney, Agent, or Firm—Leon Gilden

[57] ABSTRACT

An apparatus in use with a cardiac monitoring organization that includes a wire separator module, with a series of parallel through-extending bores directed therethrough, wherein the bores include conically flared forward and rear end portions and a medially positioned central bore to secure a wire directed therethrough in a spaced organized relationship. A modification of the module includes a groove orthogonally directed through a longitudinal axis medially of the module diametrically bisecting the bores, with a resilient securement tether receivable within the groove to permit repositioning of the wire directed therethrough. A further modified module includes a rib base defining a plurality of parallel channels therethrough, including a cover flap of a "J" shaped configuration, wherein the flap includes a "U" shaped mounting flange, with the flange including a projection receivable within a slot formed within the floor of the base.

1 Claim, 4 Drawing Sheets

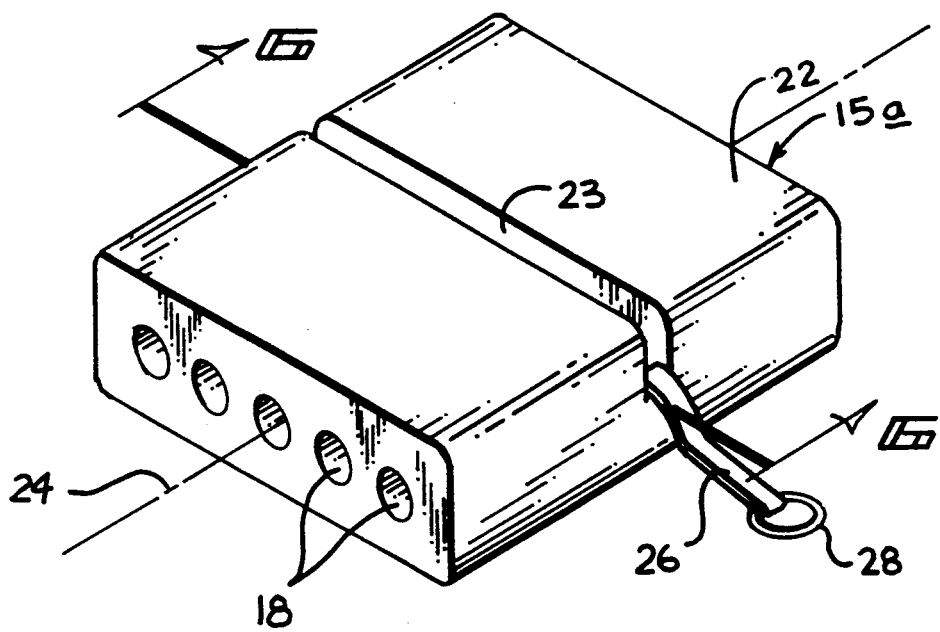
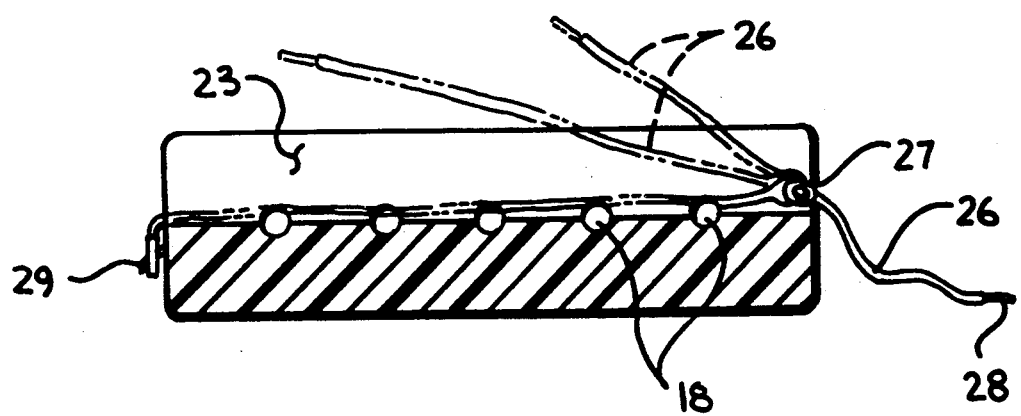

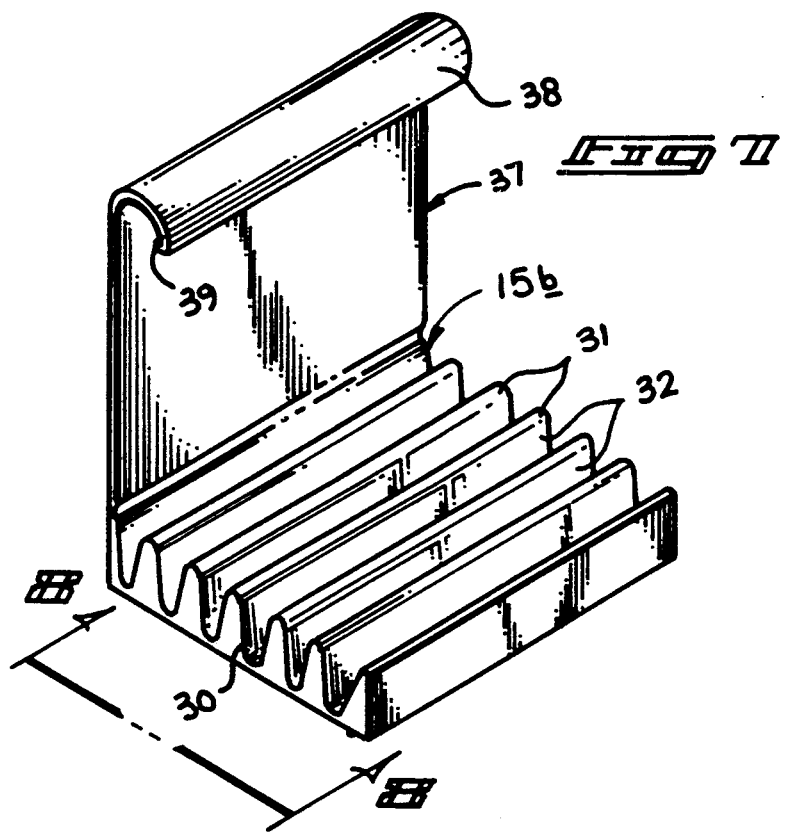
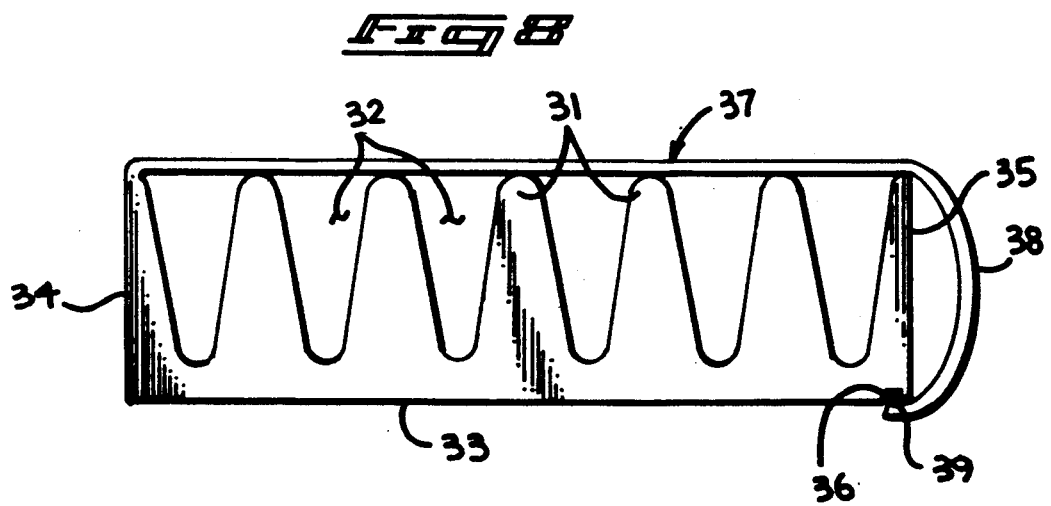

WIRE SEPARATOR APPARATUS

BACKGROUND OF THE INVENTION

1. Field of the Invention

The field of invention relates to wire loom apparatus, and more particularly pertains to a new and improved wire separator apparatus wherein the same provides positioning and registration of wires in an organized tangle-free relationship.

2. Description of the Prior Art

Wire separator devices of various types have been utilized in the prior art to provide an organized relationship of wires of a central loom, as exemplified by U.S. Pat. No. 4,584,829 to Heinke wherein a thread separator device directs various threads of a central unit to effect spaced repositioning of the threads during their transition through the separator organization.

U.S. Pat. No. 4,733,866 to Herbert sets forth a string alignment jig for utilization in alignment of various string members, such as in the stringing of tennis rackets and the like.

U.S. Pat. No. 4,412,662 to Rutecki provides for a spool member utilizing a top member mounted to a flange of the spool to direct a wire removed from the spool.

U.S. Pat. No. 4,389,024 to Sanders sets forth a strand packaging organization to secure and position strands within a package for transport.

U.S. Pat. No. 4,322,041 to Schuller sets forth a method and apparatus for winding packages utilizing various harnesses and the like for directing strands therethrough.

As such, it may be appreciated that there continues to be a need for a new and improved wire separator apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of wire separator apparatus now present in the prior art, the present invention provides a wire separator apparatus wherein the same utilizes a module in cooperation with a heart monitoring organization to position terminal ends of connector wires in use by the heart monitoring device. As such, the general purpose of the present invention, which will be described subsequently in greater detail, is to provide a new and improved wire separator apparatus which has all the advantages of the prior art wire separator apparatus and none of the disadvantages.

To attain this, the present invention includes an apparatus in use with a cardiac monitoring organization that includes a wire separator module, with a series of parallel through-extending bores directed therethrough, wherein the bores include conically flared forward and rear end portions and a medially positioned central bore to secure a wire directed therethrough in a spaced organized relationship. A modification of the module includes a groove orthogonally directed through a longitudinal axis medially of the module diametrically bisecting the bores, with a resilient securement tether receivable within the groove to permit repositioning of the wire directed therethrough. A further modified module includes a rib base defining a plurality of parallel channels therethrough, including a cover flap of a "J" shaped configuration, wherein the flap includes a "U" shaped mounting flange, with the flange including a projection receivable within the slot formed within the floor of the base.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved wire separator apparatus which has all the advantages of the prior art wire separator apparatus and none of the disadvantages.

It is another object of the present invention to provide a new and improved wire separator apparatus which may be easily and efficiently manufactured and marketed.

It is a further object of the present invention to provide a new and improved wire separator apparatus which is of a durable and reliable construction.

An even further object of the present invention is to provide a new and improved wire separator apparatus which is susceptible of a low cost of manufacture with regard to both materials and labor, and which accordingly is then susceptible of low prices of sale to the consuming public, thereby making such wire separator apparatus economically available to the buying public.

Still yet another object of the present invention is to provide a new and improved wire separator apparatus which provides in the apparatuses and methods of the prior art some of the advantages thereof, while simultaneously overcoming some of the disadvantages normally associated therewith.

Still another object of the present invention is to provide a new and improved wire separator apparatus wherein the same is utilized to position and align a matrix of wires in an orderly array adjacent free terminal ends of the wires to permit convenience of connection and positioning of the terminal ends of the wires.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an isometric illustration of a modified wire separator apparatus utilized by the instant invention.

FIG. 6 is an orthographic view, taken along the lines 6—6 of FIG. 5, in the direction indicated by the arrows.

FIG. 7 is an isometric illustration of a yet further modified module utilized by the instant invention.

FIG. 8 is an orthographic view, taken along the lines 8—8 of FIG. 7 in the direction indicated by the arrows.

DESCRIPTION OF THE PREFERRED EMBODIMENT

Figure 1:
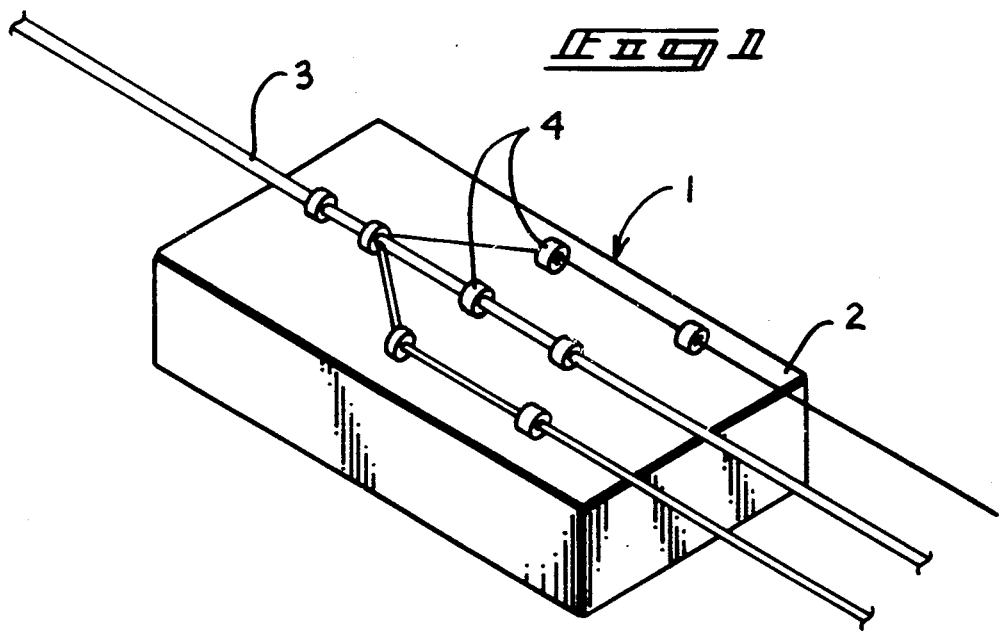
FIG. 1 is an isometric illustration of a prior art wire separator apparatus.
Figure 2:
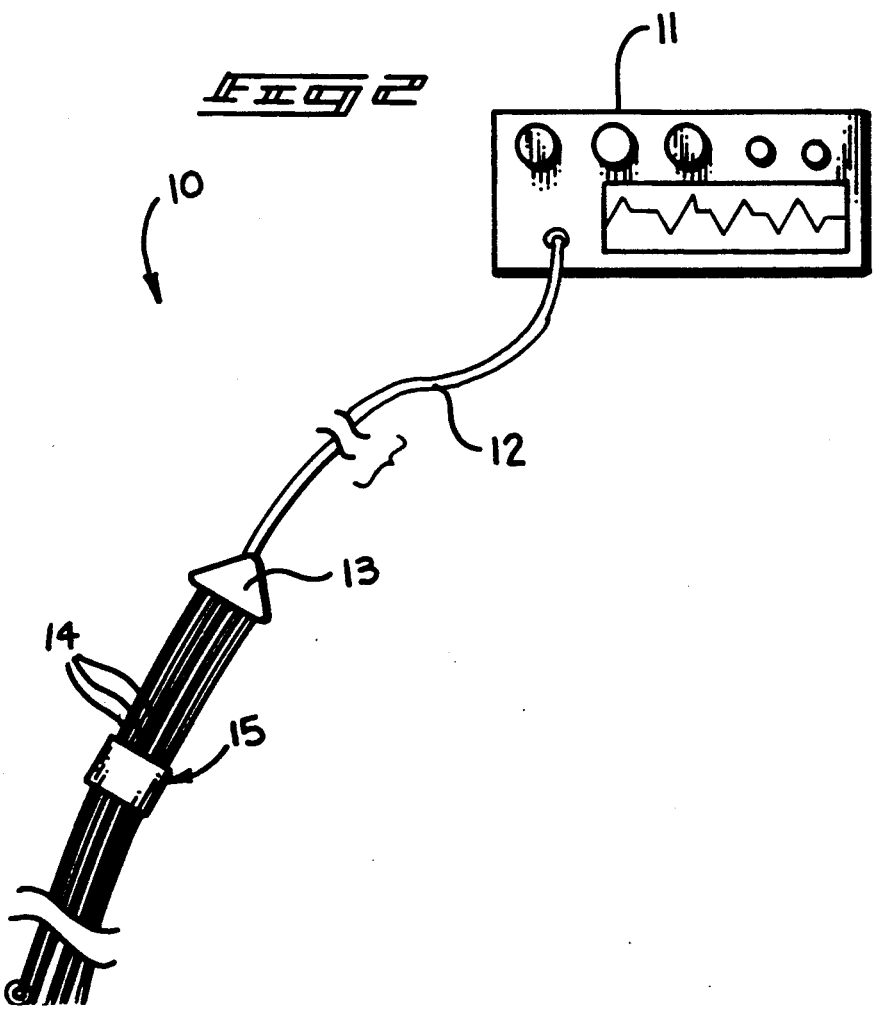
FIG. 2 illustrates the wire separator apparatus in cooperation with the heart monitoring device utilized by the instant invention.
Figure 3:
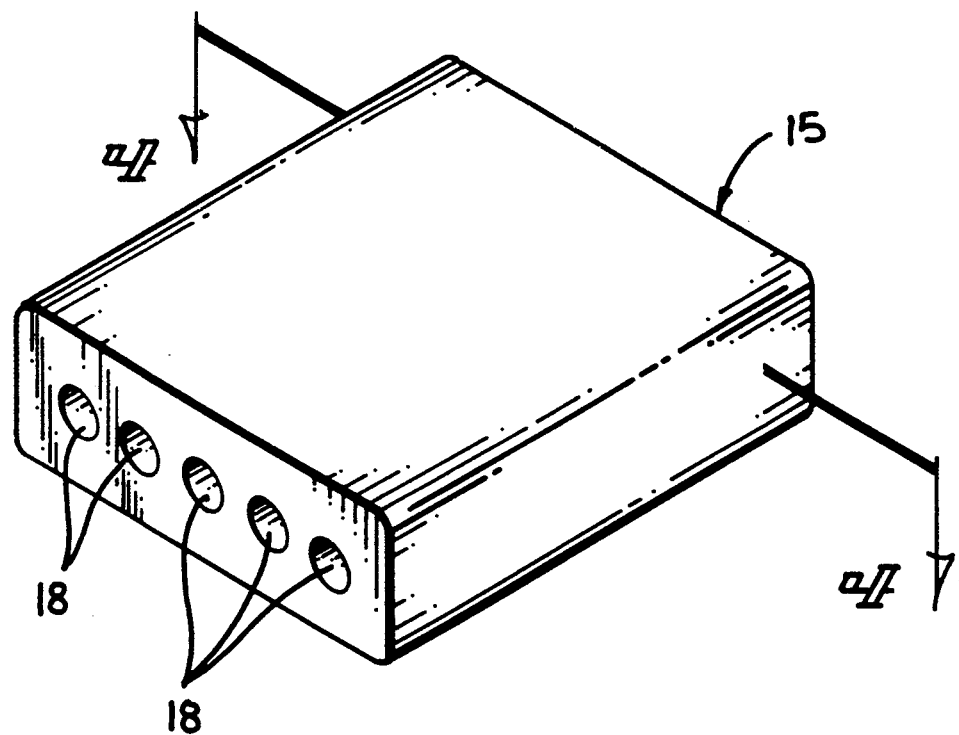
FIG. 3 is an isometric illustration of the wire separator apparatus utilized by the instant invention.
Figure 4:
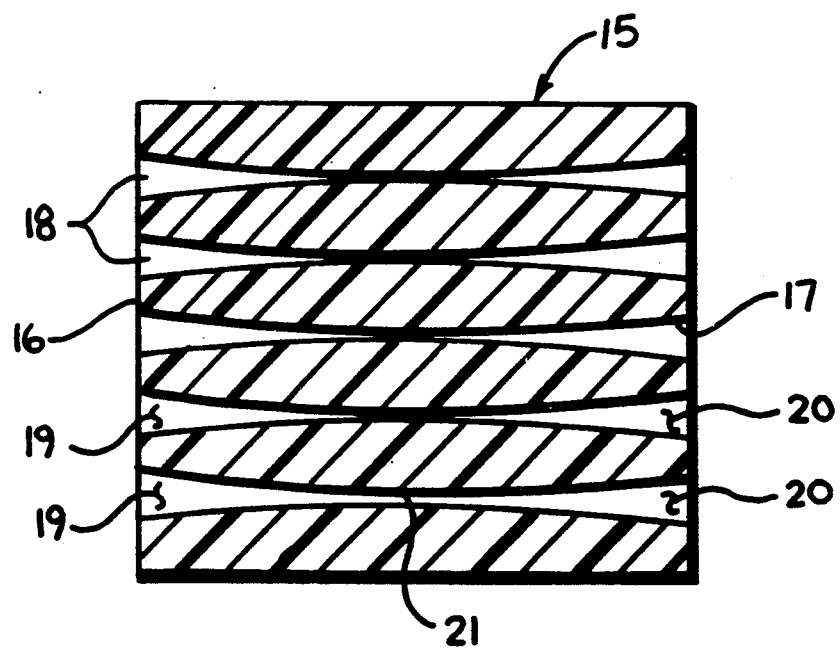
FIG. 4 is an orthographic view, taken along the lines, 4—4 of FIG. 3, in the direction indicated by the arrows.

With reference now to the drawings, and in particular to FIGS. 1 to 6 thereof, a new and improved wire separator apparatus embodying the principles and concepts of the present invention and generally designated by the reference numeral 10 will be described.

FIG. 1 illustrates a prior art wire separator apparatus 1, wherein a thread body 3 has its individual thread separated directed through guides 4 that are mounted to the support block 2, in a manner as set forth in U.S. Pat. No. 4,584,829.

More specifically, the wire separator apparatus 10 of the instant invention essentially comprises an organization utilized in a heart monitoring environment, wherein a monitoring device 11 includes a wire loom 12 that directs a series of wire leads 14 from a wire harness 13 in a spaced parallel relationship. The wire leads 14 include connector loops 14a for positioning and securement of the free terminal ends of each of the wire leads to various sending units to be monitored by the monitoring device 11. The wire leads 14 are separated in a convenient and orderly fashion by a wire separator module 15 that includes a forward end wall 16 spaced from and parallel a rear end wall 17. The module 15 includes a longitudinally aligned axis 24, in a manner as illustrated in FIG. 5. A series of parallel through-extending bores 18 are directed orthogonally through the rear and forward end walls 17 and 16 respectively and arranged relative parallel to the longitudinal axis 24. Each of the bores 18 includes a central bore 21, with a conically flared forward end portion 19 positioned in communication with the forward end wall 16 and a conically flared rear end portion 20 in communication with the rear end wall 17.

A modified module 15a, as illustrated in FIG. 5, includes a top wall 22, with a groove 23 orthogonally directed through the top wall medially bisecting and orthogonally arranged relative to the longitudinal axis 24 diametrically bisecting the bores 18. A resilient securement tether 26 is pivotally mounted to an axle 27 adjacent a right side wall of the modified module 15a, with the tether including a securement ring 28 mounted to a forward free end of the tether spaced from the axle 27. The tether 26 is received within the groove 23 and secured upon its stretching to a second position to permit its securement to a hook member 29 between a first retracted position, as illustrated in solid lines in FIGS. 5 and 6. In this manner, the modified module 15a permits easier longitudinal adjustment of each of the wire leads 14 longitudinally through the modified module 15a to position the module as desired adjacent the connector loops 14a. In use, the module is frequently mounted to a supporting surface in a conventional manner utilizing mechanical or adhesive fasteners (not illustrated).

A further modified module 15a is illustrated in FIGS. 7 and 8. The module 15a includes a support base 30, wherein the base 30 includes a plurality of parallel ribs 31 orthogonally mounted to the base defining a plurality of parallel ribs 31 orthogonally mounted to the base defining a plurality of parallel channels 32 therethrough for mounting the wires therewithin. The channels are narrowed at a lowermost end for capturing each wire therewithin. The support base 30 is defined by a base floor 33, including a base rear wall 34 orthogonally mounted to the base floor and a forward end wall 35 arranged parallel to the rear end wall 34. A floor groove 36 is coextensive with the floor 33 adjacent to and spaced from the base forward end wall 35. A "J" shaped cover lid 37 is hingedly mounted coextensively with an upper terminal end of the base rear end wall 34 and extends to overlie the ribs and channels 31 and 32 and includes a "U" shaped mounting flange 38 arranged to overlie the base forward end wall 35 when in a secured position relative to the base floor 33 to include a flange projection 39 mounted at a free end of the "U" shaped mounting flange 38 spaced from the elongate planar extent of the lid 37. In this manner, flexure of the "U" shaped mounting flange relative to the longitudinal planar extent of the "J" shaped lid 37 permits the flange projection 39 to extend overlying the forward end wall 35. Further, the "U" shaped mounting flange 38 is in itself susceptible of deformation to permit the flange projection 39 and the free end of the flange 38 to extend over the lower terminal end of the forward end wall 35 in securement and latching of the flange projection 39 within the floor groove 36, as illustrated.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A wire separator apparatus connected to a monitoring device, wherein the wire separator apparatus includes a wire loom directed therefrom, with the wire loom including a harness mounted at a terminal end of the wire loom spaced from the monitoring device, with a plurality of wire leads directed from the harness, with each of the wire leads including a connector loop mounted at a free terminal end of each wire lead, and a wire separator module means adjustably mounted to the wire leads for securement of the wire leads in a spaced parallel relationship adjacent the connector loops, and the wire separator module includes a forward end wall spaced from and parallel to a rear end wall, a top wall spaced from and parallel to a bottom wall, and a right side wall spaced from a left side wall, and a plurality of through-extending parallel bores directed through the module from the forward end wall coextensively through the end wall, and the module including a longitudinal axis orthogonally oriented relative to the forward and rear walls, with the bores arranged parallel to the longitudinal axis, and each of the parallel bores includes a conically flared forward end portion adjacent and in communication with the forward end wall, and a conically flared rear end portion positioned and in communication with the rear end wall, and a central cylindrical bore in communication with the conically flared forward and rear end portions, and the top wall includes a groove directed through the top wall and orthogonally oriented relative to the longitudinal axis, the groove diametrically bisecting each of the parallel bores, and a resilient securement tether mounted within the groove to secure the wire leads within the wire separator module, and wherein the tether includes an axle positioned adjacent the right side wall, and the tether including a first length less than that defined by a groove length defined by the groove, wherein the tether is stretched to a second length substantially equal to the groove length, and the tether includes a securement ring mounted at a free end of the tether spaced from the axle, and a hook member mounted to the left side wall to permit securement of the securement ring to the hook member.

* * * * *